United States Patent
Haas et al.

(10) Patent No.: US 6,399,800 B1
(45) Date of Patent: Jun. 4, 2002

(54) PROCESS FOR THE PRODUCTION OF FATTY ACID ALKYL ESTERS

(75) Inventors: Michael J. Haas, Oreland, PA (US); Scott Bloomer, Bloomington, MN (US); Karen Scott, Ambler, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/400,799

(22) Filed: Sep. 22, 1999

(51) Int. Cl.[7] .............................................. C07C 51/00
(52) U.S. Cl. ....................... 554/156; 554/156; 554/157; 554/195
(58) Field of Search ................................ 554/175, 176, 554/156, 157, 195

(56) References Cited

U.S. PATENT DOCUMENTS

| | | | |
|---|---|---|---|
| 2,360,844 A | 10/1944 | Bradshaw et al. | 260/410.9 |
| 2,383,601 A | 8/1945 | Keim | 260/410.9 |
| 2,494,366 A | 1/1950 | Sprules et al. | 260/410.9 |
| 4,164,506 A | 8/1979 | Kawahara et al. | 260/410.9 |
| 5,495,033 A | 2/1996 | Basu et al. | 554/1 |
| 5,520,708 A | * 5/1996 | Johnson et al. | 44/388 |
| 5,525,126 A | 6/1996 | Basu et al. | 44/308 |
| 5,624,883 A | 4/1997 | Basu et al. | 504/116 |

FOREIGN PATENT DOCUMENTS

GB  1391906  * 4/1975  ............. C11B/3/06

OTHER PUBLICATIONS

Marvin W. Formo, "Ester Reactions of Fatty Materials", *Journal of the American Oil Chemists Socitey*, vol. 31, pp. 548–559, 1954.

Stern et al., "Preparation of Methyl and Ethyl Esters from Crude Vegetable Oils and Soapstock", *American Oil Chemists Society*, Cannes, France, Nov. 3–8, pp. 420–422, edited by A.R. Baldwin, Champaign, IL, 1985.

* cited by examiner

*Primary Examiner*—Deborah Carr
(74) *Attorney, Agent, or Firm*—M. Howard Silverstein; John D. Fado; G. Byron Stover

(57) ABSTRACT

A method for producing fatty acid alkyl esters from a feedstock, involving:

(a) saponifying the feedstock with an alkali to form a saponified feedstock, (b) removing the water from the saponified feedstock to form a dried saponified feedstock containing no more than about 10% water, (c) esterifying the dried saponified feedstock with an alcohol in the presence of an inorganic acid catalyst to form fatty acid alkyl esters even with water present at levels up to about 3 wt %, and (d) recovering the fatty acid alkyl esters.

22 Claims, 3 Drawing Sheets

PROCESS FOR THE PRODUCTION OF FATTY ACID ALKYL ESTERS

BACKGROUND OF THE INVENTION

Simple fatty acid alkyl esters produced from fats and oils are being investigated in numerous settings as replacements for petroleum-derived materials, particularly diesel fuel. This invention relates to the production of fatty acid alkyl esters by a novel process. The process uses inexpensive reagents and simple technologies to quickly and efficiently produce fatty acid esters. The process involves (a) saponifying a feedstock (e.g., soy soapstock) with an alkali to form a saponified feedstock, (b) removing the water from the saponified feedstock to form a dried saponified feedstock containing no more than about 10% water, (c) esterifying the dried saponified feedstock with an alcohol by acid catalysis to form fatty acid alkyl esters, and (d) recovering the fatty acid alkyl esters. The process unexpectedly avoids elevated temperatures and pressures and incomplete esterification of all fatty acids in the starting material, and relatively long incubation times of known processes.

There is continued and growing interest in the use of renewable resources as feedstocks for replacements of petroleum-derived chemicals. It has long been known that diesel engines can use the triglycerides in fats and oils as fuels. However, their use eventually results in engine failure. This problem is alleviated by conversion of the fatty acids found in natural lipids into their simple esters, usually methyl or ethyl esters. An increasing body of evidence indicates that these esters perform well in essentially unmodified diesel engines and that, relative to petroleum-diesel fuel, they can reduce the output of particulate and hydrocarbon pollutants. The term biodiesel is applied to these esters, which are also being explored as replacements for nonrenewable chemicals in other applications, including cleaning agents, fuel additives, and substitutes for organic solvents.

Refined triglyceride oils have been the predominant feedstocks for the synthesis of biodiesel to date. However, such triglycerides are relatively high in cost, and result in a product that cannot compete economically with petroleum-derived diesel fuel. This has fostered investigation of the use of lower-value lipids, primarily animal fats and waste greases, as feedstocks. Soapstock, a lipid-rich byproduct of vegetable oil refining, is another relatively inexpensive source of fatty acids. It contains substantial amounts of glycerides, phosphoglycerides, and free fatty acids, the latter as their sodium, or less commonly potassium, salts. From soybeans, the predominant source of edible oil in the United States, soapstock is generated at a rate of about 6% of the volume of crude oil produced, amounting to as much as nearly one billion pounds of soapstock annually. Compared to refined oils, soapstock represents an inexpensive source of fatty acids since its price can be as low as one-tenth that of refined vegetable oil.

While there are several possible feedstocks for biodiesel production, it is notable that, relative to the use of e.g. waste grease as a feedstock, soapstock is a potentially attractive source of simple fatty acid esters. This is because (a) its production is relatively centralized, eliminating the need for a collection infrastructure, and (b) soapstock is not routinely subjected to the potentially damaging, extended, repeated high temperature regimes typical of waste greases.

Some methods for the production of fatty acid methyl esters (FAME) from soapstock have been reported (Stern, R., et al., Preparation of Methyl and Ethyl Esters from Crude Vegetable Oils and Soapstock, Proceedings: World Conference on Emerging Technologies in the Fats and Oils Industry, edited by A. R. Baldwin, American Oil Chemists' Society, Champaign, 1986, pp. 420–422; Sonntag, N. O. V., Fat Splitting, Esterification, and Interesterification, in Bailey's Industrial Oil and Fat Products, edited by D. Swern, Vol. 2, 4th edn, J. Wiley and Sons, New York, 1982, pp. 97–173; Haas, M. J., and K. M. Scott, J. Am. Oil Chem. Soc., 73: 1393–1401 (1996)). For example, one commerical process employs various feedstocks (e.g., soapstock-derived acid oils with free fatty acid levels up to 60%) to synthesize fatty acid esters by esterifying the feedstocks in the presence of methanol or ethanol for 10–12 hours at temperatures of 100°–120° C. (which implies the use of a pressurized system). In addition, U.S. Pat. No. 5,525,126 discloses production of fatty acid esters from soapstock by utilizing barium and calcium acetates as catalysts at temperatures of 200°–220° C. for 1–3 hours in a pressurized system. Furthermore, Formo (J. Am. Oil Chem. Soc., 31:548–559 (1954)) disclosed that several hours reflux are required to obtain high degrees of esterification of free fatty acids. However, the prior art methods have disadvantages which include their use of elevated temperatures and pressures, incomplete esterification of all fatty acids in the starting material, and/or relatively long incubation times.

There have apparently been no reports of using inexpensive reagents and simple technologies to quickly and efficiently produce fatty acid esters from feedstocks such as soapstock, both to address the economic challenges facing biodiesel and to provide new routes for soapstock utilization. The process of the present invention unexpectedly avoids elevated temperatures and pressures, incomplete esterification of all fatty acids in the starting material, the need to eliminate all water from the reaction mixture, and the relatively long incubation times of the prior art.

SUMMARY OF THE INVENTION

We have discovered a method for producing fatty acid alkyl esters from a feedstock, involving:

(a) saponifying the feedstock with an alkali to form a saponified feedstock, (b) removing the water from the saponified feedstock to form a dried saponified feedstock containing no more than about 10% water, (c) esterifying the dried saponified feedstock with an alcohol and an inorganic acid catalyst to form fatty acid alkyl esters (even when the reaction mixture contains up to about 3% water), and (d) recovering the fatty acid alkyl esters.

DETAILED DESCRIPTION OF THE INVENTION

Figure 1A:
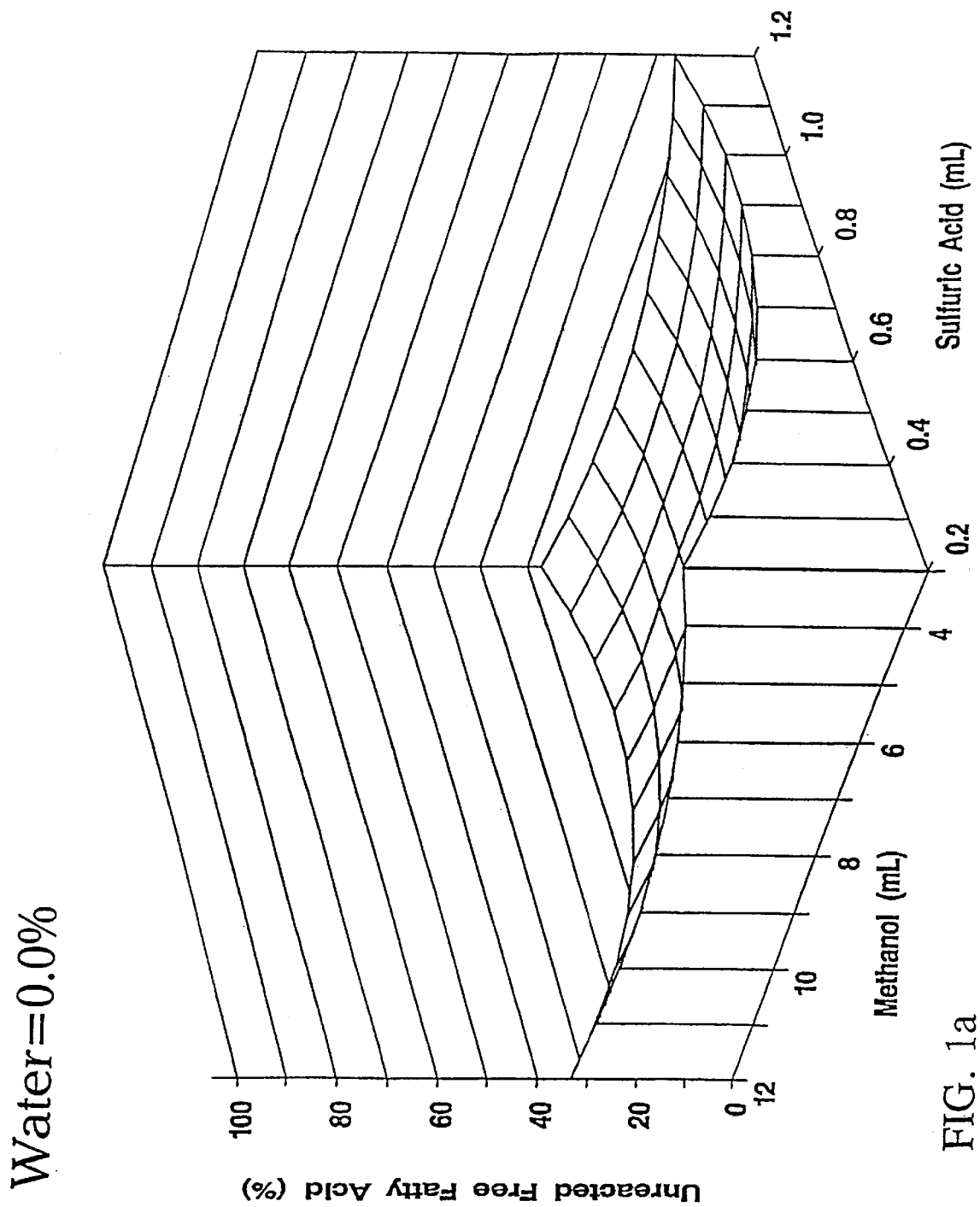
FIG. 1 shows the predicted response surfaces for the production of fatty acid methyl esters from saponified soy soapstock (2.85 g dry wt) at 35° C. and ambient pressure as a function of the amounts of methanol and sulfuric acid. Results are expressed as the percentage of free fatty acids that remained unesterified at the end of a two hour incubation. Residual water contents of the soapstock: (A) 0%, (B) 4.6%.

The process described herein is not feedstock-limited and is expected to achieve highly efficient fatty acid alkyl ester synthesis using soapstock (from crude vegetable oils) or other mixtures of vegetable lipids derived from any source of vegetable oil including, but not limited to, soy, coconut, corn, cotton, flax, palm, rapeseed/canola, safflower, and sunflower seeds or fruits; in addition, animal fats and waste greases may also be used as the feedstock. The preferred feedstock for the process of the present invention is soy soapstock because soybeans are the predominant oilseed processed in the United States, making soybean soapstock the predominant soapstock.

We have employed inexpensive feedstocks in the process of the present invention. One of these is soapstock, a by-product of the production and refining of edible vegetable oils. In the production of edible vegetable oils, a crude vegetable oil is first produced, often by extraction of oilseeds with hexane. To refine this crude oil, an aqueous solution of alkali (e.g., NaOH) is added (Summary and Recommendations, O. L. Brekke, T. L. Mounts, and E. H. Pryde, p. 562 in Handbook of Soy Oil Processing and Utilization, D. R. Erikson, E. H. Pryde, O. L. Brekke, T. L. Mounts, and R. A. Falb (eds.), published jointly by the American Soybean Association, St. Louis, Mo., and the American Oil Chemists'Society, Champaign, Ill., 1980)). This causes the separation of a material known as soapstock which contains the salts of free fatty acids (soaps) that were present in the crude oil, as well as other components of the crude oil (e.g., phospholipids, pigments, tocopherols, and sterols), and some acylglycerides and water.

Fatty acid alkyl esters may be prepared from the feedstock according to the following process:
(a) saponifying a feedstock with an alkali to form a saponified (hydrolyzed) feedstock,
(b) removing the water from the saponified feedstock to form a dried saponified feedstock containing no more than about 10% water,
(c) esterifying the dried saponified feedstock with an alcohol and an inorganic acid catalyst to form fatty acid alkyl esters, and
(d) recovering the fatty acid alkyl esters.

The feedstock is saponified with an alkali to form a fully saponified feedstock (fully hydrolyzed feedstock; that is, one in which all fatty acid ester bonds have been hydrolyzed, converting all lipid-linked fatty acids to free fatty acids). Soapstock is normally quite alkaline, with pH values between 10 and 11. Relatively little additional alkali is required to achieve fall saponification of the fatty acid esters in soapstock; sufficient alkali is added to raise the pH of the soapstock to approximately 13.5. The reaction proceeds readily and is preferably conducted under atmospheric pressure. Generally, an aqueous solution of NaOH is utilized as the alkali, though an aqueous solution of KOH can also be used. It is preferred to use as concentrated a solution of alkali as possible since this minimizes the amount of added water that must be subsequently removed. Generally a 50% (weight basis) solution of NaOH is employed. Complete saponification of the soapstock can be achieved under a variety of conditions of alkali concentration (e.g., 8 to 15.5 wt %), incubation temperatures (e.g., 40° to 100° C.), and incubation times (e.g., 2 to 72 hr). The alkali concentration, incubation temperature and incubation time must be sufficient to saponify the soapstock; one skilled in the art can readily determine these conditions. For example: If an incubation temperature of 40° C. is employed, sufficient NaOH is required to give a final concentration of 11 wt % in which case full saponification will be achieved with a 72 hr incubation. At 60° C., full saponification is achieved in 5 hr with a minimum NaOH concentration of 15.5 wt %. At 93° to 100° C., full saponification is achieved in 2 to 4 hr with a minimum NaOH concentration of 8.1 wt %. The 100° C. incubation temperature is preferable since it quickly achieves full fatty acid hydrolysis, eliminates the need for precise temperature monitoring and control if steam is used as the heat source, requires less alkali, requires less acid in subsequent steps, introduces less water into the reaction, and generates lower amounts of sodium sulfate product.

The next chemical reaction of the method of the present invention is the acid catalyzed esterification of alcohol to the free fatty acids (produced by the saponification), thus forming fatty acid esters. Since the esterification reaction is inhibited by large quantities of water, it is necessary to remove the water from the soapstock after saponification and to remove water from any unreacted methanol recycled to the reactor in order to conduct acid-catalyzed esterification. Fortunately, water removal by such means as falling film evaporation, freeze drying or analogous methods is relatively straightforward, inexpensive, and readily achieved by those skilled in the technology of fats and oils. Generally, about 100% (e.g., 100%) of the water is removed from soapstock, though the presence of up to about 10% (e.g., 10%) or up to about 5% (e.g., 5%) of water after lyophilization is not detrimental to the process of the present invention. The dried saponified soapstock can be readily pulverized by standard grinding or milling technologies to a fine powder (e.g., particle sizes 1–2 $mm^2$) which facilitates the subsequent esterification reaction.

The resulting dried saponified feedstock is then esterified with an alcohol by means of inorganic acid catalysis to form fatty acid alkyl esters (where alkyl is straight chain $C_{1-6}$, preferably $C_{1-2}$, more preferably $C_1$). The alcohol used in the process of the present invention is a $C_{1-6}$ straight chain alcohol, such as methanol or ethanol. Preferably the alcohol is methanol which reacts with free fatty acids to form methyl esters. The preferred choice of methanol as the co-reactant alcohol was based on its affordability and the fact that the majority of investigations of the suitability of fatty acid esters as diesel fuels have involved methyl esters. It is expected that the reactions described herein will also work efficiently with $C_{1-6}$ straight chain alcohols other than methanol, such as ethanol. The inorganic acid catalyst used is a mineral acid, generally sulfuric acid.

Surprisingly, the presence of about 3 wt % water in the reaction mixture (saponified feedstock, alcohol, inorganic acid catalyst) does not prevent the extremely high yields of fatty acid alkyl esters that were obtained. This water could be introduced into the reaction mixture in the form of incompletely dried saponified feedstock (as noted above, 10% water could remain after lyophilization) or it could be introduced in the other reactant (methanol) or the catalyst (inorganic acid).

The esterification reaction proceeds surprisingly quickly at moderate temperatures (e.g., about 25°–50° C. (e.g., 25°–50° C.), preferably about 30°–40° C. (e.g., 30°–40° C.), more preferably about 35° C. (e.g., 35° C.)); such moderate temperatures reduce the energy requirements of the reaction. Higher temperatures (e.g., up to 200° C.) may be utilized but are not preferred; for example, temperatures of up to the boiling point of the alcohol (e.g., 65° C. for methanol) may be utilized. Esterification surprisingly proceeds rapidly and with high degrees of completion at atmospheric pressure; greater than atmospheric pressure may be utilized (e.g., up to about 20 atm), though atmospheric pressure is preferred. The reaction time may be up to about 50 hours (e.g., 50 hours), preferably up to about 10 hours (e.g., 10 hours), more preferably up to about 5 hours (e.g., 5 hours); surprisingly good results are obtained with reaction time of up to about 2 hours (e.g., 2 hours), preferably up to about 1 hour (e.g., 1 hour), more preferably up to about 0.5 hour (e.g., 0.5 hour). Thus, at 35° C. and atmospheric pressure, surprisingly greater than 95% of theoretical maximum product was formed within the first 10 minutes of reaction; surprisingly a final yield in excess of 99% of theoretical maximum esterification was achieved within two hours of incubation (additional time may be required when the alcohol is not methanol). The typical esterification reaction temperature of 35° C. is below the boiling point of the alcohol reactant, thus no allowances need be made to recover large amounts of volatilized alcohol. The alcohol generally employed was typically a high purity (99%) grade alcohol. The concentration of sulfuric acid is generally 94%–96% (e.g., 95.9%). It is expected that less pure or concentrated grades of reactants will function in a manner proportional to their concentrations and purities. The present invention does not require, and generally does not utilize, catalysts such as barium and calcium acetates. In addition, reflux technology is not required and is generally not utilized.

Using the reactants specified above, and catalyzing the saponification step with NaOH at a final concentration of 11%, the optimal molar ratio of fatty acids: methanol: sulfuric acid at the beginning of the esterification reaction in order to achieve esterification of greater than 99% of the free fatty acids present is 1:30:2.5. The molar ratio of fatty acid to methanol consistent with this degree of conversion can range from 1:22–48; the molar ratio of fatty acids to sulfuric acid can range from 1:2–3.

Under the optimal conditions described herein (i.e., molar ratio of fatty acids: methanol: sulfuric acid=1:30:2.5), methanol was present in a 30-fold molar excess over the concentration of fatty acids. This excess fostered complete and rapid reaction, even in the presence of water levels at least as high as about 3 wt % (e.g., 3.02 wt %), which could be introduced to the reaction mixture as incompletely dried soapstock (about 10% water), as a methanol/water mixture (about 5% water), or as a component of the sulfuric acid catalyst. Excess unreacted methanol can be recovered and used in subsequent esterification reactions, increasing the efficiency of the process. The optimal requirement for a 2.5-fold molar excess of sulfuric acid to achieve complete reaction is most likely due to the need to also neutralize the substantial alkaline content of the saponified soapstock before conditions sufficiently acidic to catalyze esterification are achieved. As described above, if the saponification were conducted at 100° C., the NaOH concentration can be reduced from 11% to 8.1%; consequently the amount of sulfuric acid required in the subsequent esterification reaction would be proportionately reduced.

The process of ester synthesis from an alcohol and a fatty acid necessarily generates water and it is known that water inhibits further ester formation. Unexpectedly, the process described herein is able to achieve virtually complete esterification of the free fatty acids despite this production of water during the esterification reaction; furthermore, this is true even when the reaction mixture contains as much as about 3 wt % (e.g., 3.02 wt %) water at the onset of reaction.

Under the conditions described above, a solid byproduct is generated during the esterification reaction. When sodium hydroxide was used as the saponification catalyst, and sulfuric acid as the esterification catalyst, this solid is sodium sulfate resulting from the reaction of these two reagents with one another. There is interest in the use of potassium hydroxide, rather than sodium hydroxide, in the production of soapstock, because wastes from the process have potential use as fertilizer (Daniels, R., Agrotech to Convert Soapstock into Fertilizer, *INFORM* 6:421–423 (1995); Hodgson, A. S., Alkali Refining of Soybean Oil Using KOH, *INFORM* 6:425–426 (1995)); it is conceivable that potassium sulfate generated during the synthesis of fatty acid alkyl esters from such soapstock might have a similar potential.

The sodium sulfate, and some materials present in the saponified soapstock, partition into the solid fraction that forms during the reaction, and should not retard use of the product fatty acid alkyl esters as biodiesel or in other applications. Without being bound by theory, it is possible that sodium sulfate acts here to remove both residual water in the saponified soapstock and the water generated during esterification, allowing the esterification to proceed to a high degree of completion.

A substantial proportion (60% of theoretical maximum yield) of the fatty acid ester formed during the esterification reaction separates spontaneously from the alcohol (e.g., methanol) rich reaction mixture. This ester floats to the top of the reaction mixture during a brief period of standing following the esterification incubation, and can be readily recovered (e.g., by use of a separatory funnel or other suitable methods known in the art). The remaining fatty acid ester was located primarily in the sodium sulfate solid phase that formed during esterification and was readily released by washing with alcohol (e.g, methanol). Thus, for example, the solid material was shaken for 35 min in three times its volume of methanol. Following centrifugation to remove the solids, the liquid portion of this wash was recovered, and the alcohol (e.g, methanol) removed under reduced pressure, resulting in recovered fatty acid ester. A further small portion of ester was recovered by repeating this wash, after which the residual ester remaining in the solid fraction was only 2% of the total fatty acid alkyl ester.

The following examples are intended only to further illustrate the invention and are not intended to limit the scope of the invention as defined by the claims.

EXAMPLES

Chemicals: Soapstock was produced by alkali refining of crude soybean oil using sodium hydroxide (Summary and Recommendations, O. L. Brekke, T. L. Mounts, and E. H. Pryde, p. 562 in Handbook of Soy Oil Processing and Utilization, D. R. Erikson, E. H. Pryde, O. L. Brekke, T. L. Mounts, and R. A. Falb (eds.), published jointly by the American Soybean Association, St. Louis, Mo., and the American Oil Chemists'Society, Champaign, Ill., 1980). Triolein, 1,3-diolein, 1-monoolein, free fatty acids, L-α-phosphatidylinositol, L-α-phosphatidylethanolamine and L-α-phosphatidylglycerol for use as reference standards in high performance liquid chromatography (HPLC) were obtained from Sigma (St. Louis, Mo.). Reference L-α-phosphatidylcholine was from Avanti Polar Lipids (Alabaster, Ala.). A mixture of fatty acid methyl esters whose composition reflected the fatty acid content of soy oil (RM-1, Matreya, Inc., Pleasant Gap, Pa.) was used as a standard for calibrating detector response in HPLC. A reference standard for free fatty acids was prepared by mixing palmitic, stearic, oleic, linoleic, and linolenic acids (Sigma Chemical Co., St. Louis) in amounts proportional to their mass abundance in soybean oil (Fritz, E., and R. W. Johnson, Raw Materials for Fatty Acids, in Fatty Acids in Industry-Processes, Properties, Derivatives, Applications, edited by R. W. Johnson and E. Fritz, Marcel Dekker, N.Y., 1989, pp. 1–20). Organic solvents for use in HPLC were B&J Brand™ High Purity Grade (Burdick & Jackson, Inc., Muskegon, Mich.). Methanol was dried over sodium sulfate before use. Sulfuric acid (96.3%) was the product of Mallinkrodt Baker (Paris, Ky.).

Saponification of soapstock: Sodium hydroxide solution (50 wt %) was added to soapstock at a rate of 223 gm per kg, and the mixture was incubated at 40° C. for three days. Prior to esterification, water was removed from the saponified soapstock by lyophilization.

Optimization of the esterification reaction: A Central Composite Response Surface design (Box, G. E. P., et al., Statistics for Experimenters, Wiley, N.Y., 1978) was employed to coordinately investigate the effects and interactions of methanol and sulfuric acid concentrations, and residual water in the saponified soapstock, on the efficiency of esterification. Each reaction contained 2.85 g of dried saponified soapstock. Incubation was for two hours at 35° C. with shaking in 20 mm (diam.)×150 mm screw-capped tubes. The amounts of fatty acid methyl ester (FAME) and of residual unesterified free fatty acids were then determined by HPLC of hexane extracts. Preliminary studies identified the values of the experimental variables that gave high and low degrees of esterification, and the settings of these variables in the statistically designed experiment were then chosen to give substantial degrees of conversion. These settings were as follows: methanol: 3, 4.8, 7.5, 10.2, 12 mL; sulfuric acid: 0.2, 0.4, 0.7, 1.0, 1.2 mL; water content of saponified soapstock (mass basis): 0, 1.1, 2.5, 3.9, 4.6%.

Production of FAME at optimal conditions: To determine the time course of the esterification reaction using optimal ratios of reactants, a series of 20×150 mm screw-cap tubes containing 2.85 g (dry wt.) of saponified soapstock, 7.0 mL methanol and 0.68 mL sulfuric acid were incubated with shaking at 35° C. At selected times, tubes were withdrawn, extracted with hexane, and the FAME and free fatty acid contents of the extracts determined by HPLC.

Scaled-up esterification reactions were conducted to produce FAME for analysis and to validate the predictions of the statistically designed experiment. Fully dried saponified soapstock was the feedstock. The amounts of soapstock, methanol and sulfuric acid were chosen on the basis of Equation 1 (described below) to give high degrees of esterification. The steps in a typical reaction were:

a. Saponified soapstock was dehydrated by lyophilization and passed through a 1 mm stainless steel mesh screen (any method that successfully reduces the particle size of the dried saponified soapstock to 1–2 mm² is acceptable, e.g., pulverization). The resulting small particle size of the soapstock aided solubilization in the reaction medium.

b. Dried, sieved saponified soapstock (149 g) was added to a solution of methanol (350 mL) and sulfuric acid (34 mL) containing approximately 35 glass beads (5 mm, Thomas Scientific, Swedesboro, N.J.) and incubated with shaking for 2 hr at 35° C.

Isolation of FAME, determination of its distribution in the reaction byproducts: All steps were performed at 40–45° C.

(a) Following the esterification incubation, the reaction mixture was centrifuged 10 min at 4600×g. The resulting upper liquid layer (FAME fraction) was removed, and the lower, methanol-sulfuric acid layer was poured off as a solid pellet.

(b) The FAME fraction was washed twice by gentle mixing with 28% (v:v) of its volume of water, followed by centrifugation (40 min, 4600×g).

(c) The pellet generated during the esterification reaction was washed twice by resuspension in 175 mL methanol, recovered by centrifugation (10 min, 4600× g), dried under a stream of nitrogen, and stored over a desiccant.

For determination of their compositions by HPLC, the FAME fraction was diluted in hexane, the methanol-sulfuric acid fraction was extracted with hexane, and other fractions (e.g., saponified soapstock) were extracted with hexane-0.6% acetic acid (v:v).

Analytical methods: The water content of alkali-saponified soapstock was determined by difference following lyophilization of 100 g samples to constant weight.

HPLC was conducted on a silica column to determine the contents of glycerides, phosphoglycerides, lysophosphoglycerides and free fatty acids; peaks were eluted with gradients of isopropanol and water in hexane-0.6% acetic acid (v/v), detected by evaporative light scattering, and quantitated by reference to standard curves constructed with known pure compounds (Haas, M. J., and K. M. Scott, Combined Nonenzymatic-Enzymatic Method for the Synthesis of Simple Alkyl Fatty Acid Esters from Soapstock, J. Am. Oil Chem. Soc., 73:1393–1401 (1996)).

The presence and relative proportions of fatty acid esters in the FAME product were determined by gas chromatography (GC) using a Hewlett-Packard (HP, Wilmington, Del.) Model 5890 gas chromatograph with flame ionization detector, equipped with a HP-Innowax fused silica capillary column, 30 m by 0.53 mm (internal diameter) (Juneja, V. K., et al., Heat Resistance and Fatty Acid Composition of *Listeria monocytogenes:* Effect of pH, Acidulation, and Growth Temperature, J. Food Prot., 61:683–687 (1998)). FAME assignments were made by comparison of peak retention times with those of the esters in a reference mixture whose fatty acid content matched the fatty acid content of soybean oil (Reference Mixture 15A, NuCheck Prep, Elysian, Minn.).

Analysis of the product FAME was performed by Williams Pipeline Company (Kansas City, Kans.) using ASTM Protocol E1064 for the determination of water levels, and the method of Planck and Lorbeer (Simultaneous Determination of Glycerol and Mono-, Di- and Triglycerides in Vegetable Oil Methyl Esters by Capillary Gas Chromatography, J. Chromatography A, 697:461– 468 (1995)) for free glycerin, total glycerin, and total glycerides.

Nuclear magnetic resonance (NMR) analysis was conducted on both aqueous solutions (in deuterium oxide) and organic solvent extracts (deuterochloroform) of the solid material remaining after the esterification reaction, using a Varian (Palo Alto, Calif. ) Gemini 200 MHZ spectrometer equipped with a 5 mm $H^1/C^{13}$ computer-switchable probe operating at 25° C. For carbon spectra, between 19,000 and 50,000 transients were collected, with a total recycle time of four seconds and a spectral width of 13,000 Hz. Samples were processed with a line-broadening factor of 10 Hz. Proton data was collected using 128 transients, with a total recycle time of 2.6 seconds and a spectral width of 4000 Hz.

The protein content of the solid remaining after esterification was determined, following its dissolution in water, using the BioRad Protein Assay (Bio-Rad Laboratories, Richmond, Calif.). Bovine serum albumin was used as the reference protein. The ash content of the solid was determined gravimetrically as the residual mass following heating for 15 h at 600° C. in a Thermolyne 1500 furnace (Thermolyne Corp., Dubuque, Iowa). The sodium content of the solid was determined using a Perkin-Elmer 1100B (Norwalk, Conn.) atomic absorption spectrophotometer.

Percentages are expressed on a mass basis unless indicated otherwise. Data are the averages of at least two independent runs. The results of all such replicate determinations differed by less than 5%.

Results

Characterization of saponified soapstock: The saponification method described, using 223 g of 50% sodium hydroxide per kg of soapstock and a three day incubation at 40° C., achieved full hydrolysis of all lipid-linked fatty acid ester bonds. The product of this reaction was used in all esterification reactions described here. However, if incubation is conducted at 100° C., full saponification occurs within 2 to 3 hours using only 84 g of 50% NaOH per kg soapstock; this method may be preferable, since it is quicker, requires less alkali, will consequently require less acid in subsequent steps, and will generate lower amounts of sodium sulfate byproduct.

Following saponification, the soapstock contained 51.1% water and 26.6% free fatty acids, and had a pH of 13.5. HPLC analysis indicated the absence of triglycerides, partial glycerides, phosphoglycerides and lysophosphoglycerides (minimum detection limits: glycerides: <0.04%; phosphoglycerides and lysophosphoglycerides: <0.06%).

Optimization of the esterification reaction: Preliminary studies surprisingly indicated that high degrees of fatty acid esterification could be achieved by incubation of fully saponified soapstock in acidic alcohol solutions at mild temperatures and ambient pressure. Statistical experimental design techniques were employed to determine the effects of the amounts of saponified soapstock, methanol and sulfuric acid, and of residual water in the soapstock, on the efficiency of esterification. The resulting data were analyzed to determine the best-fit second order response surface to describe the relationship between these variables and the percentage of remaining unreacted free fatty acids. That surface is described by Equation 1:

$$FFA = 87.05 - 3.95W - 7.11M - 121.72S + 0.245WM - 0.64WS + 0.5476MS + 0.579W^2 + 0.361M^2 + 63.667S^2 \quad (1)$$

where:
  FFA=free fatty acids remaining after the reaction, as a percent of their initial content.
  W=water content of the saponified soapstock (%, mass basis)
  M=amount of methanol in the reaction (mL) per 2.85 gm of dry soapstock.
  S=amount of sulfuric acid in the reaction (mL) per 2.85 gm of dry soapstock.

A repeat of this experiment yielded essentially identical results. The $R^2$ value of the equation was 0.96, indicating that it represented a good fit to the data. The relatively high values of the coefficients of most terms involving sulfuric acid indicate that variations in acid content had the greatest impact on the degree of esterification. Equation 1 allows calculations of the amounts and ratios of reactants necessary to achieve esterification. This equation predicts that, for saponified soapstock with residual water levels below about 5%, esterification will proceed successfully (giving greater than 90% of the theoretical maximum yield of fatty acid ester) when the molar amounts of methanol and sulfuric acid exceed the fatty acid content by at least 10-fold and 1.3-fold respectively. The equation further predicts that optimal conditions for esterification, yielding complete esterification of the free fatty acids, will be achieved in reactions where the molar ratio of free fatty acids to methanol is between about 1:22 and 1:48 and the molar ratio of free fatty acids to sulfuric acid is between about 1:2 and 1:3.

Figure 1B:
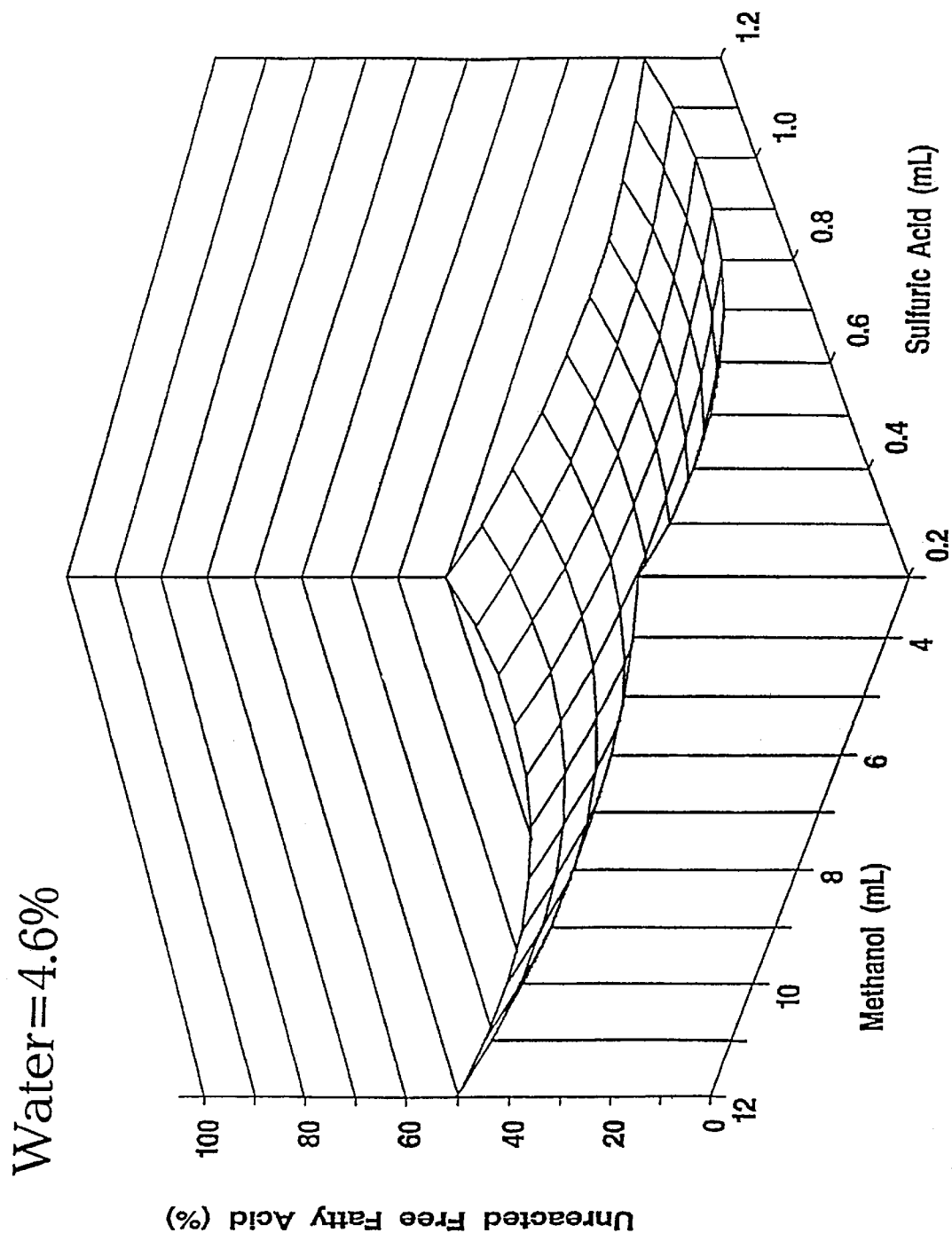

FIG. 1 shows the predicted degrees of esterification, calculated from Equation 1, as a function of the amounts of methanol and sulfuric acid in the reaction and with water contents of 0 and 4.6% in the saponified soapstock reactant. These surfaces encompass and identify reaction conditions that are predicted by Equation 1 to result in quantitative esterification (i.e., the complete conversion of free fatty acid in the reaction mixture into fatty acid methyl ester). It is notable that the reaction proceeds even when some water (at least as high as 3.02%) is present in the reaction mixture. This could be an economically attractive feature of this process, since it implies that it is not necessary to go to rigorous extremes to dry all components of the reaction or to exclude water during its conduct.

Figure 2:
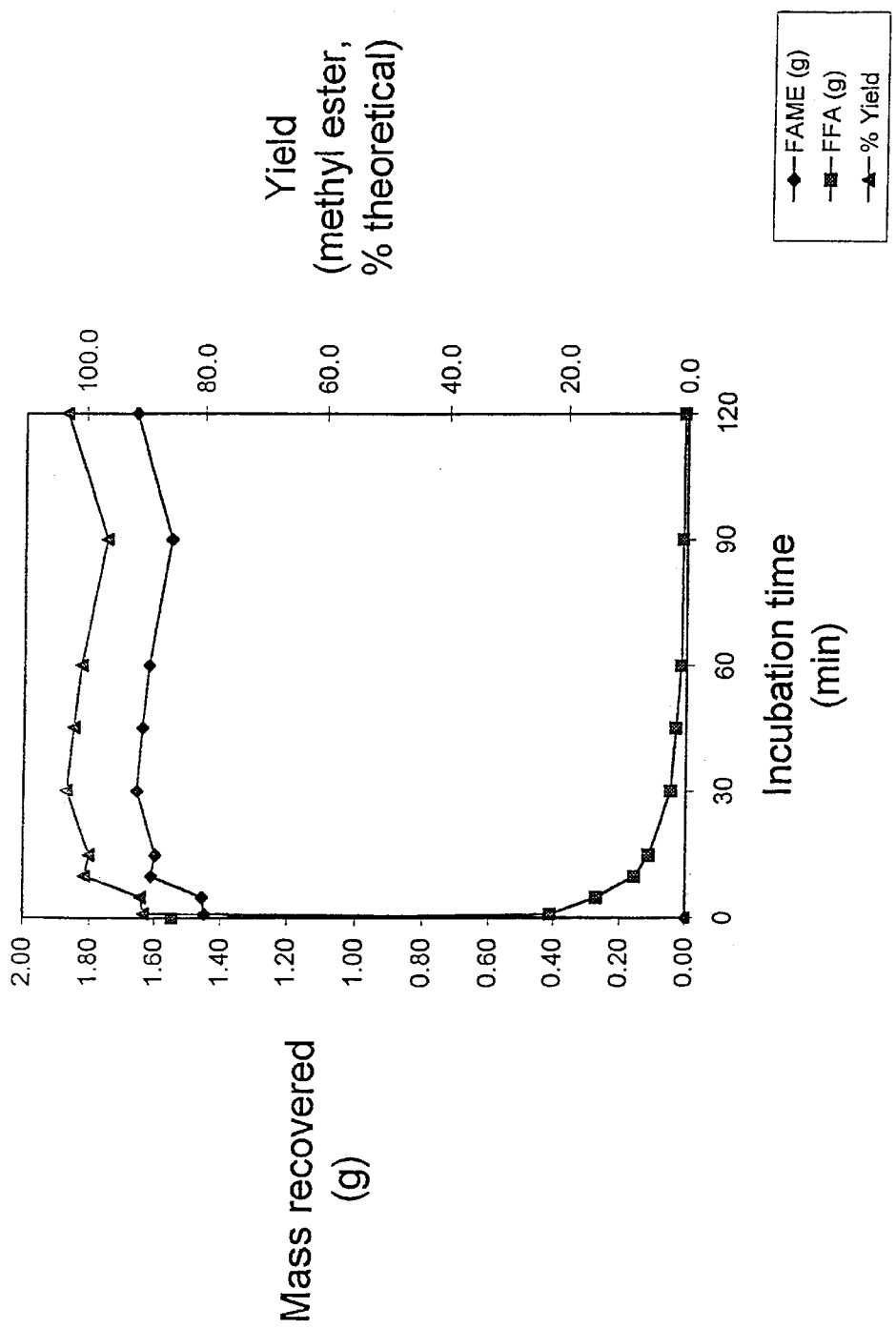
FIG. 2 shows the time course of the production of fatty acid esters, and loss of free fatty acids, during the incubation of 2.85 g dry saponified soapstock with 7.0 mL methanol and 0.68 mL sulfuric acid at 35° C. These reactant ratios are within the region predicted by FIG. 1 to give complete esterification. Points are the averages of two independent determinations; individual values differed from the average by less than 5%.

FIG. 2 illustrates the extremely rapid rate and high efficiency of this reaction at optimal substrate ratios. In this case, fully dehydrated saponified soapstock was employed, and reactant concentrations were those predicted by the response surface analysis to yield high degrees of conversion. Within the first minute of incubation the reaction surprisingly achieved 90% of theoretical maximum ester production, with a concomitant decline in the concentration of free fatty acids. Greater than 99% theoretical yield of ester was surprisingly achieved in the first 10 min of incubation.

The esterification reaction also proceeded rapidly when the saponified soapstock contained some residual water: using a sample containing 4.6% water (which is equal to 1.3% water in the reaction mixture), the degree of esterification surprisingly exceeded 99% after 10 min of incubation. Up to a water content of 3.02% in the reaction mixture (10% in the saponified soapstock), essentially quantitative esterification surprisingly occurred in two hours of incubation in reactions containing the optimal molar proportions of reactants (i.e., fatty acid: methanol: sulfuric acid=1:30:2.5).

Production of FAME under optimum conditions: To verify the predictions of the statistically designed experiment with regard to optimal ratios of reactants for full esterification, and to assess the quality of the fatty acid ester product, the esterification was conducted on a somewhat larger scale (149 g lyophilized, saponified soapstock). Following incubation, an amount of FAME equal to the theoretical maximum yield, and barely detectable traces of free fatty acids, were present in the reaction mixture; no glycerides, phosphoglycerides or lysophosphoglycerides were detected. These results are consistent with the predictions of Equation 1 and thus validate this equation.

Sixty-six mL of crude FAME were recovered directly from this reaction mixture after incubation. Following water washing, 56 mL of product were recovered, with a FAME content, determined by HPLC, of 99.2%. This represents recovery of 60% of the theoretical maximum yield of ester. The amounts of residual glycerides, glycerin, and water were below the levels currently proposed for biodiesel (Table 1). This shows the suitability of this material for use as a renewable fuel and in other applications requiring high purity fatty acid esters.

TABLE 1

Composition of Fatty Acid Methyl Esters Synthesized from Soy Soapstock, and Corresponding Proposed Specifications for Biodiesel[a]

| Property | Content Methyl Ester Product | ASTM Proposed |
|---|---|---|
| Fatty acid methyl ester (vol %) | 99.1 (wt %) | 97.0 min. |
| Total glycerides (wt %) | <0.15 | 0.2 max. |
| Free glycerin (wt %) | <0.01 | 0.02 max |
| Total glycerin (wt %) | <0.015 | 0.24 max |
| Water (wt %) | <0.04 | 0.05 max |

[a]Howell, S.A., MARC-IV, Kearney, MO, Provisional standards for biodiesel, American Society for Testing and Materials, 1998, Personal communication.

Five major peaks, constituting 98.9 % of the total peak area, were detected by GC analysis of the water-washed FAME. The retention times of these peaks were identical to those of the methyl esters of the five most common fatty acids in soy lipids: palmitic, stearic, oleic, linoleic and linolenic acids. The relative mass proportions of these esters, as indicated by GC, were 15.5, 4.4, 14.9, 56.6 and 7.7, respectively, which agrees well with the proportions of these fatty acids in soybean oil and phospholipids (Fritz, E., and R. W. Johnson, Raw Materials for Fatty Acids, in Fatty Acids in Industry. Processes, Properties, Derivatives, Applications, edited by R. W. Johnson and E. Fritz, Marcel Dekker, New York 1989, pp. 1–20; Windlholz, M. (Editor), The Merck Index, Merck & Co., Inc., Rahway, N.J., 1983, p. 779). This shows that the process described here successfully esterifies all fatty acid types found in soybean soapstock, consistent with the very high overall degree of fatty acid esterification achieved by the reaction.

Of the 40% of product FAME that did not spontaneously separate from the esterification reaction, HPLC analysis indicated that approximately 11% (expressed as % of total FAME yield) was located in the acidic methanol layer, and approximately 25% was located in the solid material present in the reaction mixture after esterification. Virtually all of the FAME in the solids fraction was released by washing with methanol; nineteen percent of the theoretical total FAME yield was located in the first wash and 4% in the second wash. The resulting methanol-washed solids retained only 2% of the total FAME. The FAME can be released from the acidic methanol layer by hexane extraction or by evaporation of the methanol (e.g., under reduced pressure).

Characterization of the solid material formed during esterification: The solid, white material formed during esterification was equal in mass to 31% of the amount of dry soapstock in the reaction. It was largely water-soluble and had an inorganic content, determined by ashing, of 69.1%. The sodium content of the solid was determined by atomic absorption spectrophotometry to be 22.6%; this equals the content predicted by assuming that its inorganic portion was sodium sulfate formed on addition of sulfuric acid to the highly alkaline soapstock. The protein content of the solid material was negligible: 0.8%. $C^{13}$-NMR spectra of aqueous solutions showed signals at 17 (—$CH_3$), 25–38 (—CH, —$CH_2$), 58–80 (complex, multiple peaks, —CHOH—), 100–104 (—CO,OH, anomeric), and 128–132 (alkene) ppm. The strong signals at 58–80 and 100–104 ppm indicate that carbohydrate was a predominant organic component of the solid. This could have originated from glycolipid in the soapstock. Proton NMR spectra of this sample were too indistinct for interpretation. $C^{13}$-NMR analysis of chloroform extracts of the solid showed strong signals at 15 (terminal methyl), 23–36 (—CH, —$CH_2$), 52 (—$OCH_3$), 128–132 (alkene), and 175 (carbonyl) ppm, consistent with the presence of FAME. Proton-NMR of the chloroform-soluble sample supported this conclusion, with peaks at 0.8 to 1 (terminal methyl), 1.2–2.9 (—CH, —$CH_2$), 3.7 (—$OCH_3$), and 5.4 (alkene) ppm.

We have thus discovered that the fatty acids in mixtures (such as vegetable oil soapstock) containing acylglycerides, phosphoglycerides, and free fatty acids, can be converted at high efficiency to fatty acid alkyl esters by a simple process that involves (1) alkali-catalyzed hydrolysis (saponification) of the fatty acid ester bonds, converting all fatty acids to the free acid form, (2) water removal, and (3) acid-catalyzed esterification in the presence of alcohol, achieving virtually quantitative esterification of the free fatty acids.

Thus, in view of the above, the present invention concerns (in part) the following:

A method for producing fatty acid alkyl esters from a feedstock, involving:

(a) saponifying the feedstock with an alkali to form a saponified feedstock, (b) removing the water from the saponified feedstock to form a dried saponified feedstock wherein the dried saponified feedstock contains no more than about 10% water, (c) esterifying the dried saponified feedstock with an alcohol and an inorganic acid catalyst to form fatty acid alkyl esters, and (d) recovering the fatty acid alkyl esters.

The above method wherein the feedstock is derived from soy, coconut, corn, cotton, flax, palm, rapeseed/canola, safflower, sunflower, animal fats, waste greases, or mixtures thereof.

The above method wherein the feedstock is soy soapstock.

The above method wherein the alkali is NaOH, KOH, or mixtures thereof.

The above method wherein the dried saponified feedstock contains about 5% water.

The above method wherein the dried saponified feedstock contains no more than about 0% water.

The above method wherein the alcohol is a straight chain $C_{1-6}$ alcohol.

The above method wherein the alcohol is methanol, ethanol, or mixtures thereof.

The above method wherein the alcohol is methanol.

The above method wherein the inorganic acid catalyst is sulfuric acid.

The above method wherein the esterifying is conducted at atmospheric pressure.

The above method wherein the esterifying is conducted at a temperature of about 25°–50° C.

The above method wherein the esterifying is conducted at a temperature of about 30°–40° C.

The above method wherein the esterifying is conducted at a temperature of about 35° C.

The above method wherein the esterifying is conducted at a reaction time of five hours or less.

The above method wherein the esterifying is conducted at a reaction time of two hours or less.

The above method wherein in (c) the molar ratio of fatty acid: alcohol is 1:22–48 and the molar ratio of fatty acid:inorganic acid catalyst is 1:2–3.

The above method wherein in (c) the molar ratio of fatty acid:alcohol:inorganic acid catalyst is 1:30:2.5.

The above method wherein in (c) about 100% of the fatty acids are esterified.

The above method wherein the esterifying is conducted in the presence of up to about 3 wt % water.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for producing fatty acid alkyl esters from a feedstock, comprising:
   (a) saponifying the feedstock with an alkali to form a saponified feedstock,
   (b) removing the water from said saponified feedstock to form a dried saponified feedstock wherein said dried saponified feedstock contains no more than about 10% water,
   (c) esterifying said dried saponified feedstock with an alcohol and an inorganic acid catalyst to form fatty acid alkyl esters, and
   (d) recovering said fatty acid alkyl esters.

2. The method according to claim 1, wherein said feedstock is derived from the group consisting of soy, coconut, corn, cotton, flax, palm, rapeseed/canola, safflower, sunflower, animal fats, waste greases, and mixtures thereof.

3. The method according to claim 1, wherein said feedstock is soy soapstock.

4. The method according to claim 1, wherein said alkali is selected from the group consisting of NaOH, KOH, and mixtures thereof.

5. The method according to claim 1, wherein said dried saponified feedstock contains about 5% water.

6. The method according to claim 1, wherein said dried saponified feedstock contains no more than about 0% water.

7. The method according to claim 1, wherein said alcohol is a straight chain $C_{1-6}$ alcohol.

8. The method according to claim 1, wherein said alcohol is selected from the group consisting of methanol, ethanol, and mixtures thereof.

9. The method according to claim 1, wherein said alcohol is methanol.

10. The method according to claim 1, wherein said inorganic acid catalyst is sulfuric acid.

11. The method according to claim 1, wherein said esterifying is conducted at atmospheric pressure.

12. The method according to claim 1, wherein said esterifying is conducted at a temperature of about 25°–50° C.

13. The method according to claim 1, wherein said esterifying is conducted at a temperature of about 30°–40° C.

14. The method according to claim 1, wherein said esterifying is conducted at a temperature of about 35° C.

15. The method according to claim 1, wherein said esterifying is conducted at a reaction time of five hours or less.

16. The method according to claim 1, wherein said esterifying is conducted at a reaction time of two hours or less.

17. The method according to claim 1, wherein in (c) the molar ratio of fatty acid:alcohol is 1:22–48 and the molar ratio of fatty acid:inorganic acid catalyst is 1:2–3.

18. The method according to claim 1, wherein in (c) the molar ratio of fatty acid:alcohol:inorganic acid catalyst is 1:30:2.5.

19. The method according to claim 1, wherein in (c) about 100% of the fatty acids are esterified.

20. The method according to claim 1, wherein said esterifying is conducted in the presence of up to about 3 wt % water.

21. A method for producing fatty acid alkyl esters from a feedstock, consisting essentially of:
   (a) saponifying the feedstock with an alkali to form a saponified feedstock,
   (b) removing the water from said saponified feedstock to form a dried saponified feedstock wherein said dried saponified feedstock contains no more than about 10% water,
   (c) esterifying said dried saponified feedstock with an alcohol and an inorganic acid catalyst to form fatty acid alkyl esters, and
   (d) recovering said fatty acid alkyl esters.

22. The method according to claim 1, wherein said feedstock is soapstock.

* * * * *